United States Patent [19]

Uffenheimer et al.

[11] Patent Number: 4,774,057
[45] Date of Patent: Sep. 27, 1988

[54] DUAL LIQUID DISPENSER PACKAGE

[75] Inventors: Kenneth F. Uffenheimer, Pelham; Keith R. Parker, Putnam Valley, both of N.Y.

[73] Assignee: Technicon Instruments Corporation, Tarrytown, N.Y.

[21] Appl. No.: 791,603

[22] Filed: Oct. 25, 1985

[51] Int. Cl.$^4$ ............................................. G01N 35/00
[52] U.S. Cl. ............................... 422/100; 422/63; 422/72; 422/102; 436/45; 436/180
[58] Field of Search ............... 206/219; 422/73, 102, 422/100, 63–65, 67, 72; 436/43, 180

[56] References Cited

U.S. PATENT DOCUMENTS

| | | | |
|---|---|---|---|
| 4,239,853 | 12/1980 | Bradley | 422/72 X |
| 4,266,559 | 5/1981 | Akhavi | 73/864.02 X |
| 4,274,885 | 6/1981 | Swartout | 422/72 X |
| 4,309,384 | 1/1982 | Trod | 422/72 X |
| 4,469,793 | 9/1984 | Guigan | 422/72 X |
| 4,515,753 | 5/1985 | Smith et al. | 422/102 |

Primary Examiner—Michael S. Marcus
Attorney, Agent, or Firm—Jeffrey M. Greenman; James J. Romano, Jr.

[57] ABSTRACT

Dual liquid dispenser package is provided and is operable to supply liquids from liquid supply chambers to liquid reservoirs through liquid supply channels by centrifugal force-induced liquid displacement and flow attendant dispenser package rotation. The supply channels include means to greatly inhibit, if not totally prevent, liquid foaming attendant liquid flow from the supply chambers to the reservoirs. Vents are included to vent the liquid supply chambers to atmosphere to prevent vacuum build-up therein, and include means preventing spillage of the liquids from the dispenser package through the vents. The dispenser package is particularly adapted for use in the supply of two reagent liquids to automated sample liquid analysis systems.

7 Claims, 5 Drawing Sheets

UNDER ROTATION

FIG. 10

QUIESCENT

DUAL LIQUID DISPENSER PACKAGE

BACKGROUND OF THE INVENTION

1. Field of The Invention.

This invention relates to a new and improved dual liquid dispenser package, which is particularly adapted for use in the supply of reagant liquids to automated sample liquid analysis systems.

2. Description of the Prior Art.

U.S. Pat. No. 4,515,753 issued May 7, 1985 to John L. Smith, et al and assigned to the assignee hereof, is the most relevant prior art known to applicant. This patent discloses an integral reagent dispenser which exhibits the capability of dispensing two liquids in the nature of reagent liquids, and is particularly adpated for use in reagent liquid supply to automated sample liquid analysis systems. Thus, and although similar in overall function to the dual liquid dispenser package of our invention, it may be understood that the reagent dispenser of U.S. Pat. No. 4,515,753, which is of "bird feeder" configuration, and is thus essentially gravity rather than centrifugal force-operated, can prove less than fully reliable under arduous operating conditions; and especially when and where called upon to operate at relatively high ambient temperatures and/or rotated at relatively high rotational velocities attendant reagent liquid supply. More specifically, it may be understood that reagent liquid spillage can occur from this prior art dispenser under these operating conditions. Too, reagent liquid spillage from this dispenser can occur attendant the required turning over, rocking, and righting of this prior art reagent dispenser to prepare the same for use in an automated sample liquid analysis system. In addition, it has been found that clogging by crystallized reagent liquid of an operationally-essential vent hole of this prior art reagent dispenser can greatly inhibit if not totally prevent the continued satisfactory operation thereof. The passages or supply troughs which supply the reagent liquids in this prior art reagent dispenser from the reagent supply chambers to the reagent dispensing wells are not, in any event, of decreasing cross-sectional area when viewed from the former to the latter, and do not include headspace; and no means of any nature are disclosed in this prior art reagent dispenser to inhibit reagent foaming.

Centrifugal feed of liquids attendant automated sample liquid analysis is disclosed in article entitled "Two-Dimensional Centrifugation for Desk-Top Clinical Chemistry" by Steven G. Schultz, et al at pages 1457–1460 of *CLINICAL CHEMISTRY*, Vol. 31, No. 9, 1985. Again, no means of any nature are disclosed in this article to inhibit liquid foaming.

OBJECTS OF THE INVENTION

It is, accordingly, an object of our invention to provide a new and improved dual liquid dispenser package.

It is another object of our invention to provide a dispenser package as above which is operable by centrifugal force-induced liquid displacement and flow from liquid supply chambers to liquid reservoirs attendant dispenser package rotation at predetermined rotational speed(s).

It is another object of our invention to provide a dispenser package as above including means which greatly inhibit, of not totally prevent, liquid foaming attendant operational liquid flow from the liquid supply chambers to the liquid reservoirs.

It is another object of our invention to provide a dispenser package as above which, for use as contemplated with aqueous liquids, comprises supply chamber vent means which are operable to prevent spillage of the liquids from the dispenser package while nonetheless venting the same to atmosphere to prevent vacuum build-up therein.

It is another object of our invention to provide a dispenser package as above which is so simply and inexpensively fabricatable from readily available, inexpensive materials as to be disposable as a practical matter after only a single utilization cycle.

It is another object of our invention to provide a dispenser package as above which is so highly reliable as to be virtually fail-safe in operation.

It is a further object of our invention to provide a dispenser package as above which is particularly adapted for use in the supply of reagent liquids in automated sample liquid analysis systems.

SUMMARY OF THE INVENTION

The new and improved dual liquid dispenser package of our invention comprises liquid supply chambers, liquid reservoirs including liquid dispensing wells spaced therefrom, and liquid supply channels independently connecting the liquid supply chambers to the liquid reservoirs for liquid flow from the supply chambers to the reservoirs. Further included are means to introduce predetermined liquid volumes to each of the liquid supply chambers; and the liquid supply chambers and liquid supply channels are respectively configured and dimensioned in accordance with those volumes to prevent liquid flow from the supply chambers to the reservoirs with the dispenser package at rest, and to provide for centrifugal force-induced displacement and flow of the liquids from the supply chambers to the reservoir through the supply channels when the dispenser package is rotated at a predetermined rotational velocity with the liquid reservoirs disposed radially outward of the supply chambers. The liquid supply channels comprise means to greatly inhibit, if not totally prevent, liquid foaming attendant liquid flow as described from the supply chambers to the reservoirs thus insuring that such flow is, at all times, substantially unimpeded, and preventing liquid back-flow from the reservoirs to the supply channels by foam-generated, syphon-like action; and these means comprise decrease in the respective cross-sectional areas of the supply channels when the same are viewed along the dispenser package in the direction from the supply chambers to the reservoirs. In at least one of the supply channels, these means further comprise the provision of headspace. Vent means are provided to vent the liquid supply chambers to atmosphere thus preventing vacuum build-up therein upon the flow of the liquids therefrom to the reservoirs; and, for use of the dispenser package of our invention as contemplated with aqueous liquids, these vent means include porous plugs of an appropriately hydrophobic material which are operable to prevent spillage of the liquids from the supply chambers through the vent means, while nonetheless admitting ambient atmospheric therethrough for venting of the supply chambers. The dispenser package of our invention is so inexpensive to fabricate, for example through use of readily moldable plastic components, as to be disposable after a single utilization cycle; and is particularly adapted for use in the supply of two reagent liquids to automated sample liquid analysis systems.

DESCRIPTION OF THE DRAWINGS

The above and other objects and significant advantages of our invention are believed made clear by the following detailed description thereof taken in conjunction with the accompanying drawings wherein.

DETAILED DESCRIPTION OF THE INVENTION

Referrring now to the application drawings, a new and improved dual liquid dispenser package configured and operable in accordance with the teachings of our invention is indicated generally at 10. In the manner of the dispenser package of U.S. Pat. No. 4,515,753, the disclosure of which is hereby incorporated in this disclosure, the dispenser package 10 comprises a base as generally indicated at 12, and a housing as generally indicated at 14 which are respectively fabricated in any appropriate manner, for example by molding, from any appropriate material, for example a generally inert inexpensive plastic. Base 12 and housing 14 respectively include complementally configured face portions 16 and 18 which are joined together at the mating upper and lower surfaces thereof by conventional adhesive or bonding techniques to form an integral dispenser package 10.

Figures 1, 2:
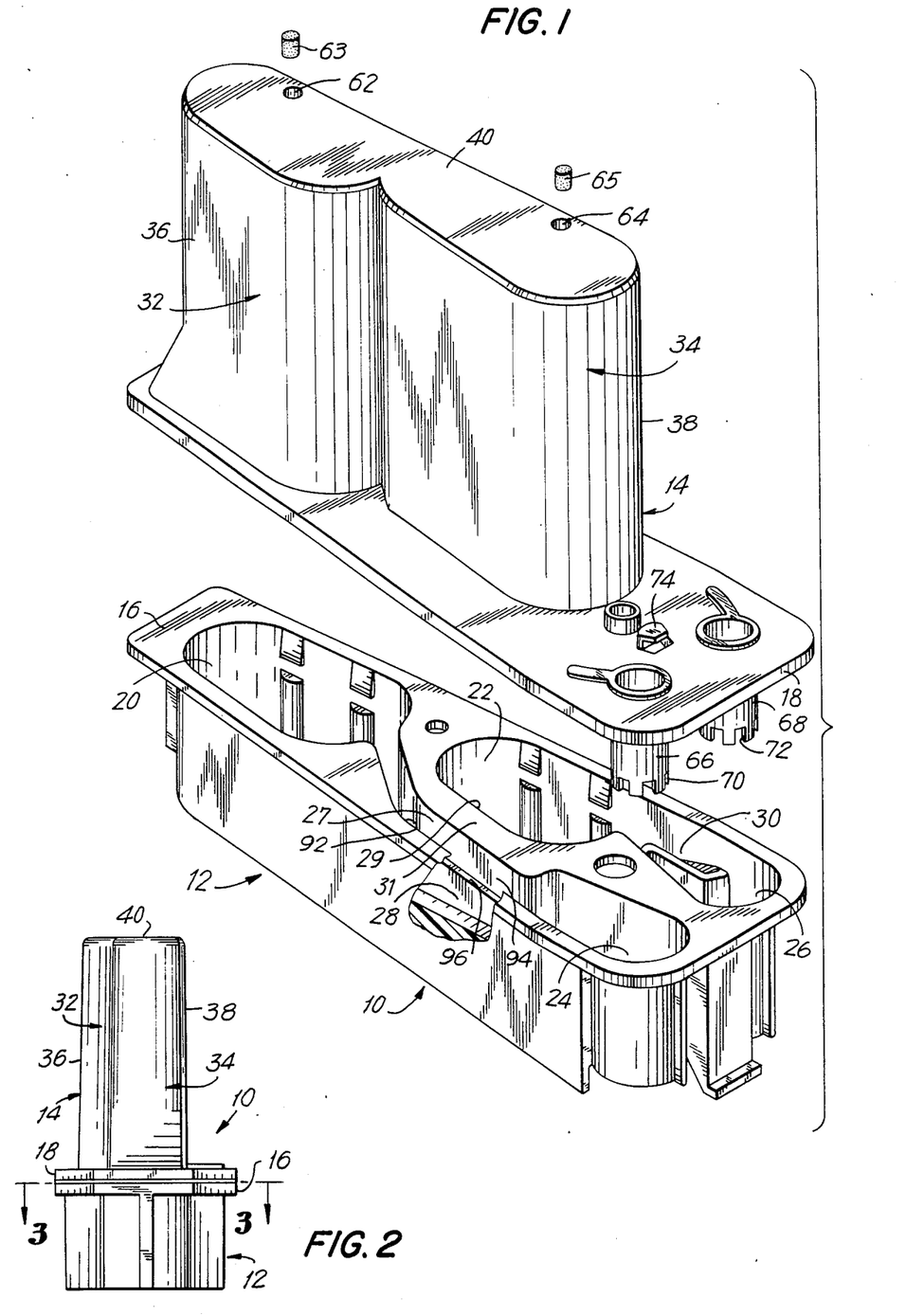
FIG. 1 is a perspective view of a new and improved dual liquid dispenser package configured and operable in accordance with the teachings of our invention, and shown disassembled and with parts cut away for purpose of clarity of illustration.
FIG. 2 is an end view of the dispenser package of FIG. 1.
Figure 3:
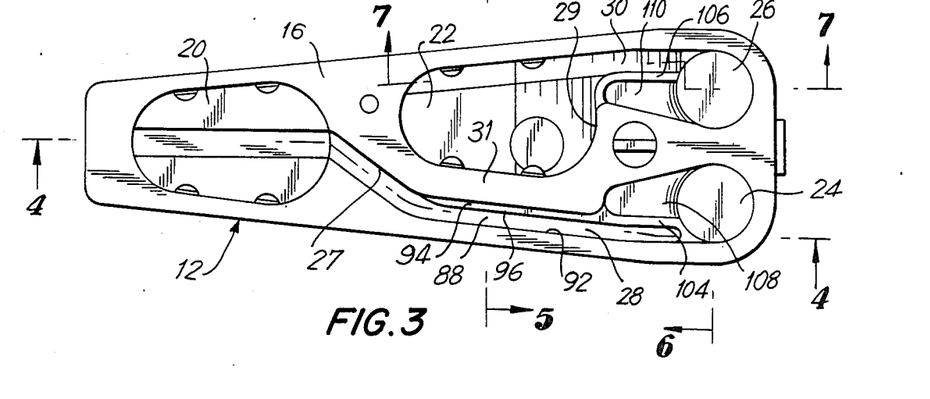
FIG. 3 is a cross-sectional view taken along line 3—3 in FIG. 2.

Base 12 includes spaced, first and second generally oval-shaped liquid supply chambers 20 and 22 formed therein as shown and respectively placed in fluid flow communication with spaced, first and second generally cylindrical liquid reservoirs 24 and 26, also formed therein as shown, by spaced, first and second liquid supply channels 28 and 30, again formed therein as shown. Fluid flow communication between supply chamber 20, supply channel 28 and reservoir 24, respectively, and supply chamber 22, supply channel 30 and reservoir 26, respectively, is prevented as shown by the relevant imperforate walls 27 and 29 of the base portion 31 as best seen in FIGS. 1 and 3.

Figure 4:
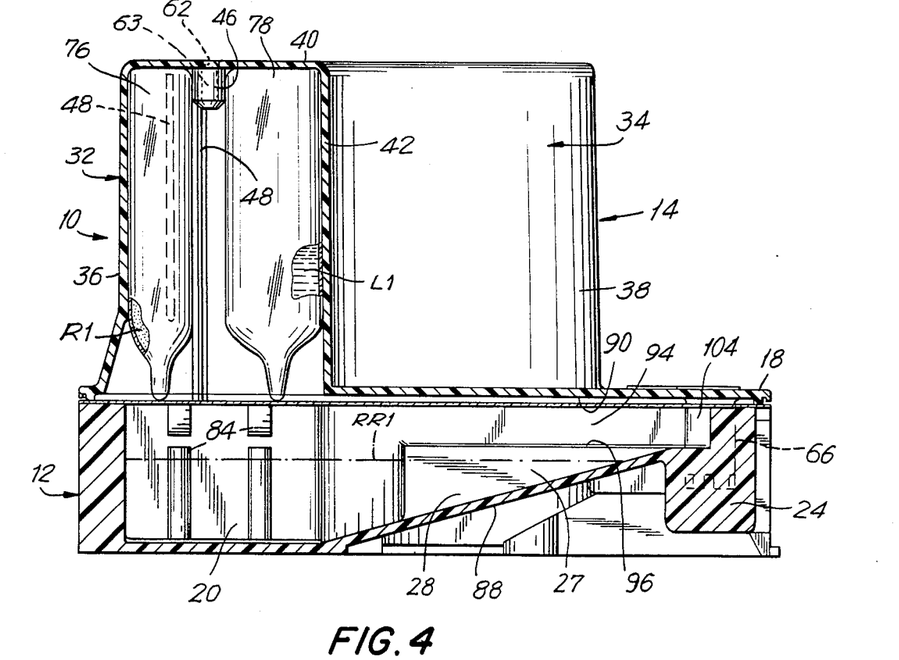
FIG. 4 is a cross-sectional view taken along line 4—4 in FIG. 3.
Figure 5:
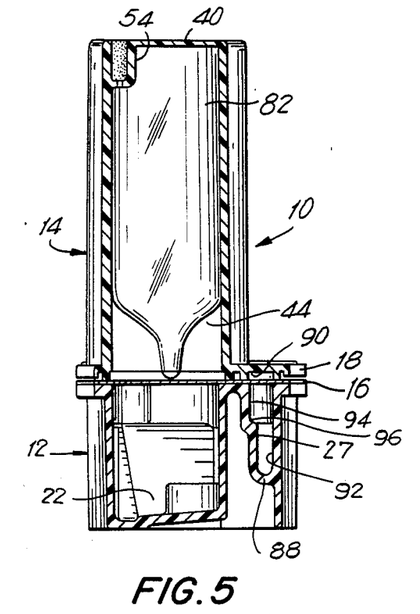
FIG. 5 is a cross-sectional view taken along line 5—5 in FIG. 3.

Housing 14 includes spaced, first and second generally oval-shaped capsule support chambers 32 and 34 formed therein as shown by flexible housing walls 36 and 38, housing top wall 40, internal housing walls 42 (FIG. 4) and 44 (FIG. 5; with fluid flow communication between capsule support chambers 32 and 34 being prevented as shown by the imperforate housing walls 42 and 44. Capsule support chamber 32 is essentially divided from a capsule support standpoint by internal rib and guide members 46 and 48 into adjacent capsule support compartments 50 and 52 as best seen in FIG 4; while capsule support chamber is essentially divided from this same standpoint by internal rib and guide members 54 and 56 into adjacent capsule support compartments 58 and 60. Vent holes 62 and 64 are formed as shown in FIG. 1 in the housing top wall 40 to vent capsule support chambers 32 and 34 to atmosphere to prevent vacuum build-up; and porous plugs 63 and 65 of any appropriately hydrophobic material are disposed therein as best seen in FIGS. 1 and 4.

Figure 6:
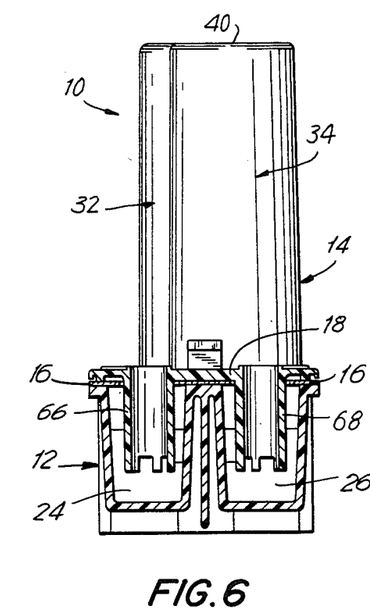
FIG. 6 is a cross-sectional view taken along line 6—6 in FIG. 3.

Further included in housing 14 are spaced, generally cylindrical dispenser wells 66 and 68 formed integrally with housing face portion 18 to extend downwardly therefrom as shown into the respective liquid reservoirs 24 and 26 upon dispenser package assembly in the manner best seen in FIG. 6. The respective lower edges of dispenser wells 66 and 68 are notched as indicated at 70 and 72 for the support of appropriate liquid filters, not shown, therefrom. Evaporation cover mounting means 74 are formed on the upper surface of housing face portion 18 for the mounting of an evaporation cover, not shown, therefrom to cover the open ends of the dispenser wells 66 and 68 when the dispenser package 10 is not in use, thereby preventing liquid evaporation therefrom.

Figure 7:
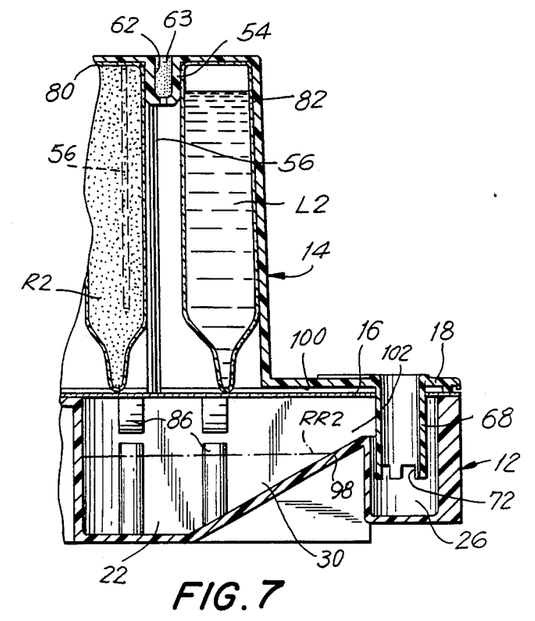
FIG. 7 is a cross-sectional view taken along line 7—7 in FIG. 3.

Capsules are indicated at 76 and 78 in FIG. 4, and at 80 and 82 in FIG. 7, and are respectively complementally configured and sized relative to capsule support chambers 32 and 34 for inserti and retention by frictional contact therein by frictional contact; with capsules 76 and 78 being retainable as shown in FIG. 4 in capsule support compartments 50 and 52 of support chamber 32, and capsules 80 and 82 being retainable as shown in FIG. 7 in capsule support compartments 54 and 56 of support chamber 34. Capsules 76, 78, 80 and 82 are made from an inert, readily breakable material, for example, glass.

For use, for example, of the dual liquid dispenser package 10 of our invention in the automated analyses of liquid samples as described in detail hereinbelow, capsules 76 and 80 would respectively contain predetermined quantities of different lyophilized sample reagent powders as indicated at R1 and R2 in FIGS. 4 and 7; while capsules 78 and 82 would respectively contain predetermined quantities of appropriate reagent powder-reconstituting aqueous liquids as indicated at L1 and L2 in FIGS. 4 and 7 for the reconstitution of the reagents R1 and R2 into liquid form upon the mixing thereof. As described in U.S. Pat. No. 4,515,753, this mixing is accomplished by the tilting of the dispenser package 10 on its back, the manual or mechanical application of sufficient force upon the flexible side walls 36 and 38 of housing 14 to break capsules 76 and 78, and 80 and 82, to release the respective contents thereof, and the gently rocking and re-righting of the package. Spillage of the aqueous liquids from the dispenser package 10 through vents 62 and 64 is prevented by the hydrophobic plugs 63 and 65 which essentially repel those liquids. This gentle rocking and re-righting of the dispenser package 10 results in the mixing, and flow under the force of gravity, of the reagent powder R1 and reconstituting liquid L1 into liquid supply chamber 20 of base 12, thereby reconstituting the reagent R1 in a known volume predetermined to partially fill the supply chamber 20 and the connected liquid supply channel 28; and results in the mixing, and flow under the force of gravity, of the reagent powder R2 and reconstituting liquid L2 into liquid supply chamber 22 of base 12, thereby reconstituting the reagent R2 in a known volume predetermined to partially fill the supply chamber 22 and the connected liquid supply channel 30 therewith. This partial filling as described of the liquid supply chambers and liquid supply channels of interest with the reconstitued reagent liquids RR1 and RR2 is illustrated in phantom at RR1 in FIG. 4 for supply chamber 20 and supply channel 28; and is illustrated in phantom at RR2 in FIG. 7 for supply chamber 22 and supply channel 30. In each instance, this partial filling as described of the respective supply chambers 20 and 22, and the supply channels 28 and 30 by the reconstituted reagent liquids RR1 and RR2 to prepare the dispenser package 10 of our invention for use as above, is to levels carefully predetermined in accordance with the respective known reconstituted reagent liquid volumes available via the capsules 76, 78, 80 and 82, and with the respective known supply chamber and supply channel volumes and configurations; and these levels are, in no instance, sufficient to result in any reconstituted reagent liquid flow into either of liquid reservoirs 24 or 26 with the dispenser package 10 level and at rest. Entry of the broken glass which results from capsule breakage into supply chambers 20 and 22 is prevented by simple plastic screen or like inserts, not shown, which are supported in supply chambers 20 and 22 from support ribs 84 and 86 above the respective levels of reconstituted reagent liquids RR1 and RR2.

Referring now in greater detail to liquid supply channel 28 which oonnects liquid supply chamber 20 to liquid reservoir 24 as described hereinabove, FIGS. 1, 3, 4 and 5 of the application drawings will be seen to make clear that the same is of decreasing cross-sectional area when viewed in the direction from supply chamber 20 to reservoir 24. This is due to the positive or upward slope, when viewed in that direction, of wall 88 of base 12 which forms the bottom wall of supply channel 28 taken, of course, in conjunction with the essentially flat or zero slope of the bottom surface 90 of edge portion 18 of housing 14 which forms the top wall of supply channel 28, and the essentially vertical and parallel orientation of the spaced walls 27 and 92 of base 12 which form the side walls of the supply channel 28.

Further included in supply channel 28 is a significant measure of headspace, or increase in cross-sectional area when viewed from bottom to top at any single location thereon, for example the cross-sectional view of FIG. 5; and it will be clear to those skilled in this art that this headspace, as indicated at 94, is provided by the cut-back 96 in base wall 27 as best seen in FIGS. 1, 3, 4 and 5. The headspace 94 is of sufficient cross-sectional area in combination with the overall decrease in the cross-sectional area of the liquid supply channel 28 to inhibit liquid foaming in tha supply channel as described hereinbelow.

Liquid supply channel 30 which connects liquid supply chamber 22 to liquid reservoir 26 is also of decreasing cross-sectional area when viewed in that direction; due, of course, to the positive or upward slope of wall 98 of base 12 which forms the bottom wall of supply channel 30, taken again in conjunction. with the essentially flat or zero slope of the bottom surface 100 of edge portion 18 of housing 14 which forms the top wall of supply channel 30, and the essentially vertical and parallel orientation of the spaced walls 29 and 102 of base 12 which form the side walls of supply channel 30, all as best seen in FIGS. 1 and 7.

Base 12 further includes upstanding, partially curved walls 104 and 106 respectively formed as best see in FIG. 3 at the respective extremities of supply channels 28 and 30 adjacent the reservoirs 24 and 26; and which, in conjunction with the slightly sloped, essentially flat adjacent walls 108 and 110 of base 12, respectively form dam-like structures and intermediate steps leading from the supply channels 28 and 30 into the reservoirs 24 and 26.

In use —for example for the automated successive multiple analyses of a series of liquid samples with regard to a variety of constituents thereof in the manner disclosed in copending application for U.S. patent Ser. No. 10,236, filed Feb. 2, 1987, which is a continuation of U.S. Pat. No. 441,881 entitled "Single Channel Continuous Flow System" filed Nov. 11, 1982 by Steve Saros, et al now abandoned, and the disclosure of which is hereby incorporated in the disclosure of this application—it may be understood that a plurality of the dual liquid dispenser packages 10 of our invention, with the respective dispenser package reagent and reconstituting liquid capsules broken as described hereinabove to result in the containment of the reconstituted reagent liquids RR1 and RR2 in the respective dispenser package supply chambers 20 and 22 as depicted in FIGS. 4 and 7 hereinabove, would be disposed in the side-by-side manner schematically illustrated in FIG. 8 on a turntable or like rotational device 112 with the respective dispenser package dispensing wells 66 and 68 disposed radially outward as shown of the respective dispenser package supply chambers 20 and 22 in each instance. For such application turntable 112 would take the form of reagent turntable 32 as depicted and described in some detail in copending application Ser. No. 441,881; and would be operatively associated as depicted in FIG. 1 of that application with the other essential analysis system components.

Figure 9:
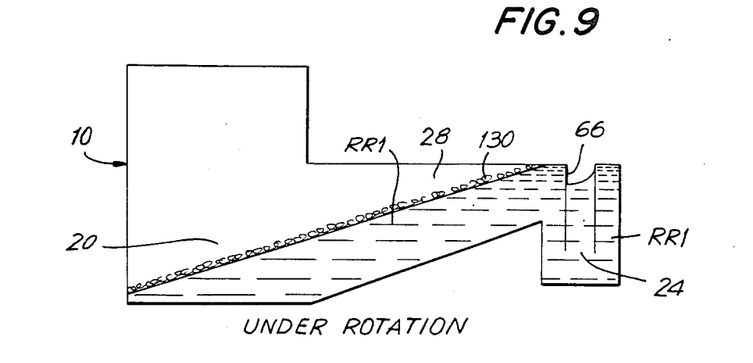
FIG. 9 is a generally schematic cross-sectional view illustrating the operational conditions of the dispenser package of FIG. 1 under rotation.
Figure 10:
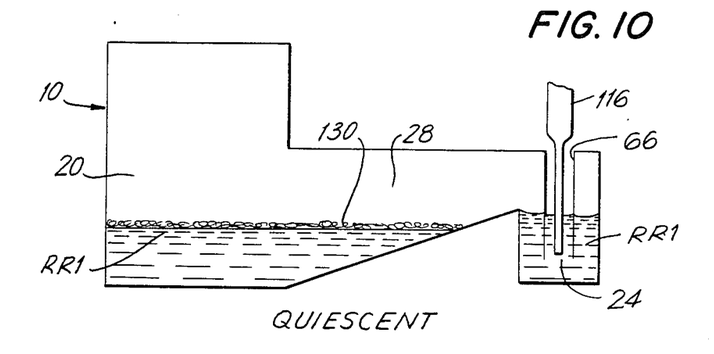
FIG. 10 is a generally schematic cross-sectional view illustrating the operational conditions of the dispenser package of FIG. 1 at rest.

Turntable 112 is initially spun at a rotational velocity and for a period of time predetermined in accordance with the essential parameters and configurations of the dispenser package supply chambers, supply channels and reservoirs, and the known volumes of the reconstituted reagent liquids RR1 and RR2 disposed in the supply chambers and channels to be sufficient to cause desired volumes of the reconstituted reagent liquids to be displaced and flow, under the influence of centrifugal force, from the resepctive supply chambers 20 and 22 through supply channels 28 and 30 over walls 104 and 106 onto steps 108 and 110 and, form the latter, into the reservoirs 24 and 26; thereby partially filling the reservoirs with those desired reagent liquid volumes to levels which are, in each instance, well above the lower ends of the dispensing wells 66 and 68. This is representatively illustrated by FIGS. 9 and 10 for flow of the reconstituted reagent liquid RR1 from supply chamber 20 through supply channel 28 to reservoir 24 of a dispenser package 10; with FIG. 9 illustrating reagent liquid displacement and flow under the influence of centrifugal force generated by rotation of turntable 112, and FIG. 10 illustrating quiescent reagent liquid conditions upon termination of turntable rotation. Although not illustrated, it will be clear to those skilled in this art that the centrifugal force-induced displacement and flow of reconstituted reagent liquid RR2 from dispenser package supply chamber 22 through supply channel 30 to reservoir 26 will be the same as that illustrated for reconstituted reagent liquid RR1.

Figure 8:
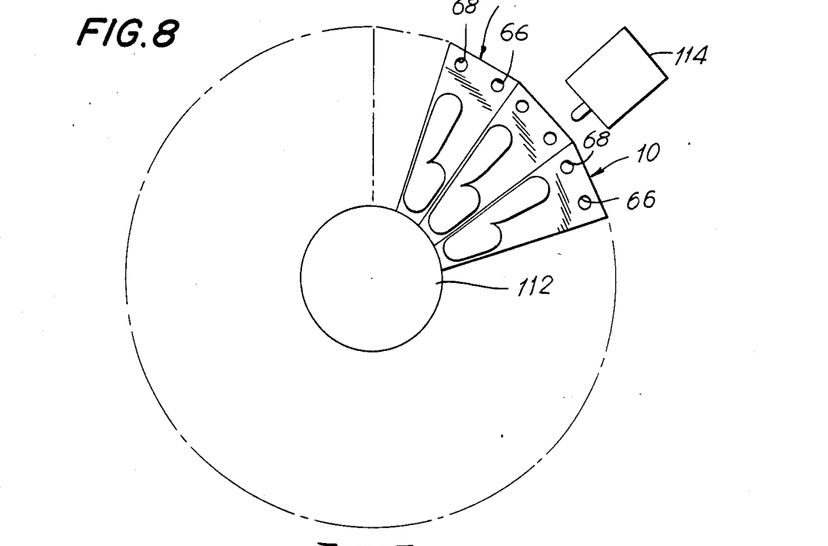
FIG. 8 is a generally schematic top view of a plurality of the dispenser packages of our invention operatively disposed on a turntable.

With the reconstituted reagent liquids RR1 and RR2 supplied as described by centrifugal force-induced displacement and flow into reservoirs 24 and 26, and thus to the respective interiors of dispensing wells 66 and 68, it will be clear that the dispenser package 10 of interest can be indexed, through appropriate intermittent rotation of turntable 112, for presentation in turn to a probe assembly as schematically indicated at 114 in FIG. 8 and withdrawal by aspiration via probe means as depicted at 116 in FIG. 10 of desired volumes of the reconstituted reagent liquids RR1 and RR2 from the dispensing wells 66 and 68 for use in sample analysis as described in detail in copending application for U.S. Pat. No. 441,881.

Replenishment of the respective reconstituted reagent liquids RR1 and RR2 in the dispenser package reservoirs 24 and 26, and thus in dispensing wells 66 and 68, may occur automatically attendant the centrifugual forces generated by indexing of the turntable 112 in accordance with the operational requirements of the sample analysis system. Alternatively, and in instances wherein this is not sufficient, turntable 112 can be periodically rotated under the control of the analysis system controller through what might be termed a "spin cycle" for reagent liquid replenishment. Vacuum build-up in the reagent supply chambers 20 and 22 attendant reagent liquid flow therefrom as described is, in any event, prevented by the porous hydrophobic plugs 63 and 65 in vents 62 and 64 which, while effective to prevent aqueous liquid spillage from the dispenser package 10 as described, are nonetheless also effective to enable the flow of ambient atmospheric air thereinto through vents 62 and 64. Upon the supply as described of all of the usable reconstituted reagent liquids RR1 and RR2 in a dispenser package 10 to the dispensing wells 66 and 68, and aspiration therefrom as described by the probe means 116, the dispenser package 10 of interest is simply discarded.

Of particularly significant advantage with regard to the new and improved dispenser package 10 of our invention is the fact that the provision of liquid supply channels 28 and 30 of decreasing cross-sectional area when viewed in the direction from liquid supply chambers 20 and 22 to liquid reservoirs 24 and 26, coupled in the case of liquid supply channel 28 which is substantially longer and thus of substantially greater overall volume than liquid supply channel 30, with the provision of the headspace 94, have been discovered to very greatly inhibit, if not totally prevent foaming of the liquid attendant the centrifugal force-induced displacement and flow thereof from the liquid supply chambers to the liquid reservoirs; it being understood by those skilled in this art that such foaming could, if left unchecked, operate to restrict liquid flow from the supply chambers to the liquid reservoirs to such an extent that the dispenser package would soon be rendered virtually useless for the disclosed purposes thereof.

Figure 11:
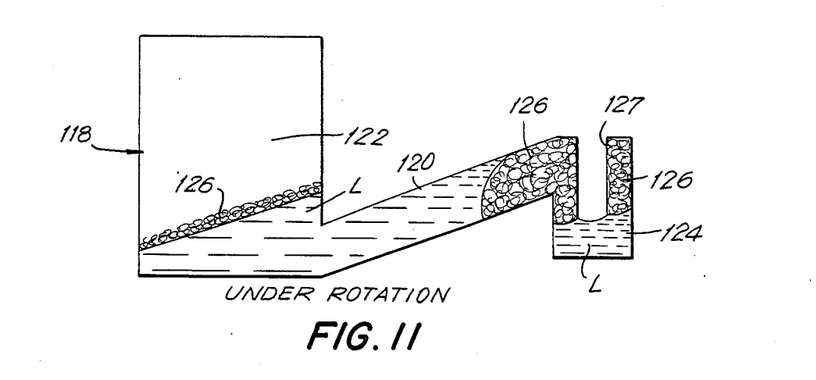
FIG. 11 is a generally schematic cross-sectional view illustrating the operational conditions of a dispenser package lacking an inventive feature of the dispenser package of our invention, and depicted under rotation.
Figure 12:
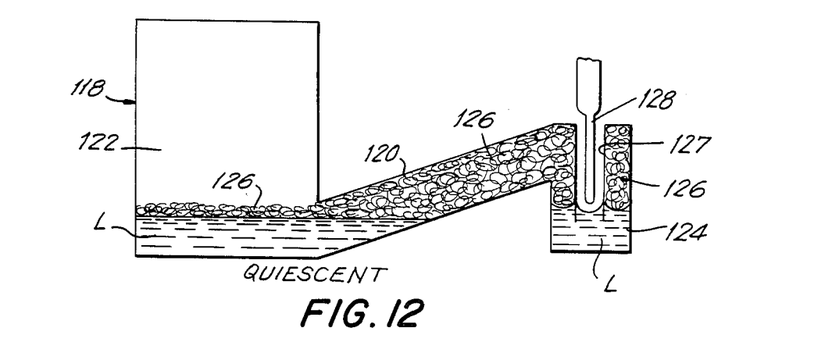
FIG. 12 is a generally schematic cross-sectional view illustrating the operational conditions of the dispenser package of FIG. 11 at rest.

More specifically, and taking for example a centrifugal force-operated dispenser package of the nature here under discussion, as indicated schematically at 118 in FIG. 11 to include a liquid supply channel 120 of constant cross-sectional area, it will be clear that with the same under rotation as depicted, the entrapment of ambient air in the liquid supply channel 120 attendant the centrifugal force-induced displacement and flow of a liquid L from a liquid supply chamber 122 to a liquid reservoir 124 will result in the generation of a significant amount of foam 126 which will, of course, significantly impede, if not totally prevent, the continued flow of the liquid L from supply chamber 122 to the reservoir, and especially under conditions wherein some significant measure of the liquid available in liquid supply chamber 122 has been depleted by removal from reservoir 124. In addition, and with the liquid L quiescent as schematically depicted in FIG. 11 upon the termination of rotation of the dispenser package, it will be clear that the foam 126 which has built up on the surface of the liquid L in each of the reservoir 124, the supply channel 120, and the supply chamber 122, can function in the nature of connecting wick-like means, via the interstitial liquid L trapped between the bubbles of the foam 126, to syphon the liquid L from the reservoir 124 through supply channel 120 back to the supply chamber 122.

In either or both of the above events, it will be clear to those skilled in this art that a totally unacceptable operational condition of dispensing package 118 will soon be reached wherein, despite both the presence of more than sufficient liquid L in liquid supply chamber 120 for the task at hand, and the best practical mechanical efforts at transfering the same by centrifugal force-induced displacement and flow to liquid reservoir 124 and the included dispensing well 127, there will simply be insufficient liquid L available in the latter for aspiration as a practical matter by a travel limited dispensing probe as shown at 128 in FIG. 11.

Referring again to FIGS. 9 and 10 of the application drawings with regard to the operation of the dispenser package 10 of our invention, FIG. 9 makes clear that even if some measure of foam, as therein indicated at 130 and somewhat exaggerated for purposes of clarity of illustration, does develop attendant the centrifugal force-induced displacement and flow of the reagent liquid RR1 from supply chamber 20 to reservoir 24, the decreasing cross-sectional area of supply channel 28, taken in conjunction with the headspace 94 (FIG. 1), will operate to effectively retain the leading edge of the foam 130 in the supply channel 28 above and in essence behind the bulk of the displaced and flowing reagent liquid RR1, thereby preventing the foam from flowing into reservoir 24 or from in any way obstructing or fully occluding the smallest cross-sectional area of the supply channel 28 as found at the juncture thereof with the reservoir 24. Thus, flow of the reagent liquid RR1 from the supply chamber 20 to the reservoir 24 is substantially unimpeded by foam 130. Upon termination of rotation of the dispenser package 10, and the return of the reagent liquid RR1 to quiescent conditions, FIG. 10 makes clear that whatever amount of foam 130 was generated attendant reagent liquid flow as described will simply lie atop the reagent liquid in the supply chamber 20 and supply channel 28 and, most importantly, without reservoir 24. Thus, syphoning of the reagent liquid RR1 from reservoir 24 back to supply chamber 20 by foam 130 is rendered impossible.

Liquid supply channel 28 which connects liquid supply chamber 22 to liquid reservoir 26 of the dispenser package 10 as described in detail hereinabove, and which is here reiterated as also being of decreasing cross-sectional area when viewed in the direction from the supply chamber to the reservoir, functions essentially as described for liquid supply channel 28 with regard to the minimization of foaming of reagent liquid RR2 attedant the centrifugal force-induced displacement and flow thereof from supply chamber 22 to reservoir 26, and with regard to the prevention of any foam which is generated attendant such liquid displacement and flow from impeding the same or syphoning the reagent liquid RR2 back from reservoir 26 to supply chamber 22. The relative shortness of liquid supply channel 28 does, however, render foaming of the reagent liquid RR2 even less likely to occur, and thus no headspace is provided therein. For use of the dispenser package 10 of our invention with more foaming-prone liquids, and/or under more foaming-prone operational conditions, it would, of course, be within the scope of our invention to provide headspace in liquid supply channel 30.

For use of the dispenser package 10 of our invention in automated sample liquid analysis systems of the nature dislcosed in copending application for U.S. patent Ser. No. 441,881 which utilize an immiscible liquid or "oil" which selectively "wets" the analysis system components to the substantial exclusion of the sample liquids, to thereby minimize sample "carryover," e.g. the contamination of a succeeding sample liquid by the residue of a preceding sample, and thereby maximize the accuracy of the sample liquid analysis results, it is contemplated by this disclosure that the dispensing wells 66 and 68 be fabricated or treated to have hydrophilic inner surfaces, thereby insuring that the reagent liquids as contained therein will each exhibit a concave meniscus for suitable surface retention of a drop of the immiscible liquid as is placed thereon to in essence form an immiscible liquid "lens," all in the manner disclosed in some detail in U.S. Pat. No. 4,515,753. Alternatively, and as also disclosed in U.S. Pat. No. 4,515,753, suitable lens yokes having hydrophobic inner surfaces may be positioned in dispensing wells 66 and 68 to the above purposes.

Although disclosed hereinabove by way of illustrative example as applied to the dispensing of reconstituted reagent liquids attendant the automated analysis of sample liquids, it will be clear to those skilled in this art that the dispensing package 10 of our invention is by no means limited to use with such liquids or for such purposes.

Various changes may be made in the herein-disclosed preferred embodiment of our invention without departing from the spirit and scope thereof as defined by the appended claims.

What is claimed is:

1. In a liquid dispenser package including, a liquid supply chamber, a liquid reservoir spaced from said liquid supply chamber, a liquid supply channel connecting said liquid supply chamber to said liquid reservoir for liquid flow from said liquid supply chamber to said liquid reservoir, and capsule means containing a predetermined volume of liquid and adapted to introduce said predetermined volume of liquid into said liquid supply chamber and said liquid supply channel, the improvements comprising, said liquid supply chamber and said liquid supply channel being configured, and defining a liquid volume relative to said predetermined liquid volume, operable to prevent liquid flow from said liquid supply chamber through said liquid supply channel to said liquid reservoir with said dispenser package at rest, and to permit centrifugal force-induced displacement and flow of said liquid from said liquid supply chamber to said liquid reservoir through said liquid supply channel upon rotation of said dispenser package at a predetermined rotational speed with said liquid reservoir disposed radially outward of said liquid supply chamber on said dispenser package, said liquid supply channel extending generally horizontally from said said liquid supply chamber to said liquid reservoir and comprising means to inhibit liquid foaming attendant centrifugal force-induced liquid flow from said liquid supply chamber through said liquid supply channel to said liquid reservoir, said liquid foaming inhibiting means comprising said liquid supply channel being of decreasing overall cross-sectional area when viewed along said dispenser package in the direction from said liquid supply chamber to said liquid reservoir, and means defining headspace in said liquid supply channel, said headspace being of sufficient cross-sectional area in combination with the overall decrease in cross-sectional area of said liquid supply channel to inhibit foaming of said liquid attendant the centrifugal force-induced flow of said liquid from said liquid supply chamber to said liquid reservoir.

2. In a liquid dispenser package as in claim 1 wherein, said headspace is defined by an increase in the cross-sectional area of the upper part of said liquid supply channel when viewed along said dispenser package in the direction from said liquid supply chamber to said liquid reservoir.

3. In a liquid dispenser package as in claim 1 further comprising, said liquid supply chamber being closed and including vent means connecting the same to atmosphere, the further improvements comprising, means in said vent means operable to prevent the flow of said liquid therethrough from said liquid supply chamber, and to permit the flow of ambient atmospheric air therethrough into said liquid supply chamber whereby, spillage of said liquid from said liquid supply chamber through said vent means is prevented, and the build-up of vacuum in said liquid supply chamber upon the flow of said liquid therefrom into said liquid reservoir is also prevented.

4. In a liquid dispenser as in claim 3 wherein, said means in said vent means comprise a hydrophobic material.

5. In a liquid dispenser package as in claim 1 further comprising, a second liquid supply chamber, a second liquid reservoir spaced from said second liquid supply chamber, and second liquid supply channel connecting said second liquid supply chamber with said second liquid reservoir for liquid flow from said second liquid supply chamber to said second liquid reservoir, said second liquid supply chamber, supply channel and liquid reservoir being respectively spaced from and unconnected with the first-mentioned of the same, and capsule means containing a second predetermined volume of liquid and adapted to introduce said second predetermined volume of liquid into said second liquid supply chamber and supply channel, the improvements further comprising, said second liquid supply chamber and said second liquid supply channel being configured, and defining a liquid volume relative to said second predetermined liquid volume, operable to prevent liquid flow from said second liquid supply chamber to said second liquid supply reservoir with said dispenser package at rest, and to permit centrifugal force-induced displacement and flow of said said liquid from said second liquid supply chamber to said second liquid reservoir through said second liquid supply channel upon rotation of said dispenser package at a predetermined rotational speed with said second liquid reservoir disposed radially outward of said second liquid supply chamber on said dispenser package, said second liquid supply channel extending generally horizontally from said second liquid supply chamber to said second liquid reservoir, and comprising means to inhibit liquid foaming attendant centrigual force-induced liquid flow from said second liquid supply chamer through said second liquid supply channel to said second liquid reservoir, said liquid foaming inhibiting means comprising said second liquid supply channel being of decreasing overall cross-sectional area when viewed along said dispenser package in the direction from said second liquid supply chamber to said second liquid reservoir.

6. In a liquid dispenser package as in claim 5 wherein, said second liquid supply channel further comprises headspace.

7. In a liquid supply system including a liquid dispenser package, means to rotate said liquid dispenser package, and means operatively associated therewith to periodically remove liquid from said liquid dispenser package, the improvements comprising, said liquid dispenser package including, a liquid supply chamber, a liquid reservoir spaced from said liquid supply chamber and including liquid dispensing means, a liquid supply channel connecting said liquid supply chamber to said liquid reservoir for liquid flow from said liquid supply chamber to said liquid reservoir, and capsule means containing a predetermined volume of liquid and adapted to introduce said predetermined volume of liquid into said liquid supply chamber, said liquid supply chamber and said liquid supply channel being configured, and defining a liquid volume relative to said predetermined liquid volume, operable to prevent liquid flow from said liquid supply chamber to said liquid reservoir with said dispenser package at rest, and to permit centrifugal force-induced displacement and flow of said liquid from said liquid supply chamber to said liquid reservoir through said liquid supply channel upon rotation of said dispenser package at a predetermined rotational speed with said liquid reservoir disposed radially outward of said liquid supply chamber, said liquid supply channel extending generally horizontally from said liquid supply chamber to said liquid reservoir and comprising means to inhibit liquid foaming attendant liquid flow from said liquid supply chamber to said liquid reservoir whereby, said dispenser package may be rotated at said predetermined rotational speed by said rotating means to displace and flow a portion of said liquid from said liquid supply chamber to said liquid reservoir through said liquid supply channel, the rotation of said dispenser package by said rotating means at said predetermined rotational speed discontinued and at least some of the thusly displaced and flowed liquid removed from said liquid reservoir through said liquid dispensing means by said liquid removal means, and said dispenser package again rotated at said predetermined rotational speed by said rotating means to displace and flow another portion of said liquid form said liquid supply chamber through said liquid supply channel to said liquid reservoir to replenish the supply of said liquid in the latter, and whereby foaming of said liquid attendant the displacement and flow thereof as described through said liquid supply channel will be inhibited.

* * * * *